United States Patent [19]

Pai et al.

[11] 4,293,692

[45] Oct. 6, 1981

[54] CONTINUOUS PROCESS FOR MANUFACTURING SUBSTANTIALLY FULLY METHYLATED SUBSTANTIALLY FULLY METHYLOLATED MELAMINE COMPOSITIONS

[75] Inventors: Venkatrao K. Pai; Joseph F. Skrivan, both of Stamford, Conn.

[73] Assignee: American Cyanamid Company, Stamford, Conn.

[21] Appl. No.: 852,380

[22] Filed: Nov. 17, 1977

[51] Int. Cl.³ .......................................... C07D 251/70
[52] U.S. Cl. .................................................. 544/196
[58] Field of Search ........................................ 544/196

[56] References Cited

U.S. PATENT DOCUMENTS 2,645,625  7/1953  Bonzagni ............................. 544/196
3,488,350  1/1970  Donaldson ........................... 544/196
3,824,232  7/1974  Pusch et al. ......................... 544/196

FOREIGN PATENT DOCUMENTS 433150  9/1975  U.S.S.R. .............................. 544/196

*Primary Examiner*—John M. Ford
*Attorney, Agent, or Firm*—Bruce F. Jacobs

[57] ABSTRACT

The manufacture of a substantially fully methylated, substantially fully methylolated melamine composition is carried out by a continuous process in which the methylolation of melamine is conducted in two stages, the first stage being effected at an acidic pH and the second stage being effected at an alkaline pH. The reaction mixture is then concentrated and reacted with methanol after which all of the unreacted volatiles and precipitated salts are removed to provide the product composition.

11 Claims, No Drawings

CONTINUOUS PROCESS FOR MANUFACTURING SUBSTANTIALLY FULLY METHYLATED SUBSTANTIALLY FULLY METHYLOLATED MELAMINE COMPOSITIONS

This invention relates to a continuous process for making substantially fully methylated, substantially fully methylolated melamine compositions. Such compositions have utility as cross-linking agents in coating compositions including those applied by spraying, brushing, dipping and the like or by use in electrodeposition coating operations. They can be used with water-dispersible non-gelled polymeric materials such as disclosed in the U.S. Pat. No. 3,471,388.

Substantially fully methylated, substantially fully methylolated melamine compositions have been known for a number of years. These compositions are fundamentally monomeric although they may contain some dimeric materials, some trimeric materials, tetrameric materials or even higher oligomer. These oligomers are formed when two or more triazine ring derivatives are joined together either through a methylene bridge or through an ether linkage which joins a pair of methylene bridges. The presence of small amounts of such oligomers in the product decreases the freezing point of the product and keeps it as a free flowing liquid at temperatures as low as 0° C. In the past, in order to obtain methylol melamines, selected mole ratios of melamine and formaldehyde were combined in an aqueous medium, heated and the resulting solution of methylol melamine was thereafter dried over long periods of time to obtain a solid product. Such processes were expensive because of the periods of time involved to dry or dehydrate methylol melamine and the additional equipment which was required to do the same. Such products are also made in a batch process without the drying step, but such a process involves lengthy stripping time to remove the excess unreacted reactants which have to be concentrated separately before recycling.

Theoretically, it is possible to methylolate melamine fully, that is, to produce hexamethylol melamine. However, frequently a composition purporting to be hexamethylol melamine, when analyzed shows a fractional degree of methylolation. It is well recognized that fractional methylolation is not possible. Thus, when a composition contains, on analysis, a degree of methylolation of 5.75, 5.80 or even 5.90, it is recognized that this is but an average degree of the methylolation of the melamine compound and that the methylol composition is composed of a preponderant amount of hexamethylol melamine with minor amounts of pentamethylol melamine and perhaps traces of tetramethylol melamine and trimethylol melamine.

The concept of averages is also applicable to the alkylation (i.e., etherification) of the hexamethylol melamine composition. Thus, there cannot be a fractional methylation and, as a consequence, when on an analysis, a given composition shows that the degree of methylation is 4.5, 5.5, or 5.9, it is considered that, in fact, there is present some trimethylether, some tetramethylether, some pentamethylether and some hexamethylether of the hexamethylol melamine.

Due to the demand for the substantially fully methylated, substantially fully methylolated melamine compositions as cross-linking agents in the coating art, a continuous process for their manufacture would be highly desirable. To date, however, no such process has been found feasible. A difficult problem associated with the perfection of such a continuous process has been the tendency of the hexamethylolmelamine formed during the methylolation reaction to crystallize out (of the reaction syrup). The crystallizing could also occur in the subsequent steps of the process such as the stripping steps. Thus, without a solution to that problem, the art has utilized only batch processes for making the compositions.

In accordance with the present invention, however, it has been found that the crystallization of the hexamethylolmelamine can be avoided by conducting the methylolation reaction in two stages, one at an acidic pH and the second at an alkaline pH. Thus, the standard aqueous batch process has used a single stage methylolation at neutral pH which produced a highly monomeric aqueous methylolated melamine syrup which had to be treated very carefully to avoid crystallization of the intractable hexamethylolmelamine.

However, in accordance with the present invention it has now been found that by conducting the methylolation reaction initially (in the first stage) at an acidic pH some oligomers are formed before the fully methylolated melamine is formed and that this mixture of monomers and oligomers has much less tendency to crystallize than the highly monomeric hexamethylolmelamine mixture. The pH of the reaction mixture is then adjusted to the alkaline side in the second stage of the methylolation whereby the methylolation of the melamine is substantially completed without further oligomerization. Thus, the methylolation step as well as the subsequent steps of the process are much easier to practice and a continuous process is practicable.

Accordingly, it is the object of this invention to provide a continuous process for the manufacture of substantially fully methylated, substantially fully methylolated melamine wherein the methylolation step is conducted in two stages, one stage being conducted at an acidic pH, preferably from 4 to 6 and the second stage being conducted at a higher pH, preferably from above 7 to about 10.

This object has been accomplished by the present invention which comprises a process having the following steps:

(1) conducting the methylolation of melamine in two stages as follows: (a) in a first stage continuously charging melamine and aqueous formaldehyde to a first reaction zone in a ratio of from about 9 to about 18 moles of formaldehyde per mole of melamine while controlling the pH of the reaction mixture thus formed in the reaction zone at from about 4 to 6 and also controlling the temperature of the reaction mixture at from about 45° to about 75° C. and the residence time of the mixture in said zone for a period sufficiently long to effect methylolation of the melamine to an average degree of about 4.5 to 5.5 with the methylolated product being from about 40% to about 70% in the oligomeric state and from about 30% to about 60% in the monomeric state; then (b) in a second stage, passing the reaction mixture from the first reactor to a second reactor and adjusting the pH of the reaction mixture to from above 7 to about 10 and holding the temperature at about 45° C. to about 75° C. for a residence time sufficient for the melamine monomers and oligomers to become substantially fully methylolated;

(2) passing the reaction mixture from the second reactor to an evaporator and removing about 70–95% of the water content thereof;

(3) passing the concentrated reaction mixture from the evaporator to a third reactor along with from about 20 to about 30 moles of methanol per mole of melamine utilized in step 1(a) while controlling the pH of the mixture at from about 1.2 to about 2.5, the temperature at about 30°–55° C. and the residence time for a sufficient period to effect an average degree of methylation of at least about 4.5;

(4) passing the reaction mixture from the third reactor into a (first) neutralization tank and adjusting the pH thereof to from about 9 to about 12;

(5) passing the mixture from the neutralization tank to a distillation column and distilling off unreacted methanol therefrom;

(6) passing the bottoms from the distillation column to a (first) stripper and removing substantially all the water and unreacted formaldehyde therefrom;

At this point in the process, the reaction mixture (bottoms) from step 6 can be sent directly to a solids separation unit to remove the precipitated process salts (after the fashion of step 10, below) and recover a methylated, methylolated melamine product having a sufficiently high methanol to melamine ratio (about 4.5) to make it satisfactory for use as a cross-linking agent in most coating compositions. However, for certain specific coating applications, a higher degree of methylation in the product is required. To provide this higher degree of methylation, steps 7, 8 and 9 may be conducted as follows:

(7) passing the bottoms from the stripper to a fourth reactor along with sufficient methanol to provide about 5–10 additional moles of methanol per mole of melamine and controlling the pH at 1.2–2.5, the temperature at from about 30° C. to about 55° C. and the residence time to a period sufficient to give an average degree of methylation of at least 5.3;

(8) passing the reaction mixture from the fourth reactor to a (second) neutralization tank wherein the pH is adjusted to 8–10;

(9) passing the mixture from the neutralization tank to a (second) stripper and removing substantially all the volatiles therefrom and finally

(10) treating the bottoms from the (second) stripper in a solids separation unit such as a rotary vacuum filter or centrifuge to remove precipitated sodium nitrate and sodium formate salts therefrom.

The invention is illustrated by the following example in which all parts are parts by weight unless otherwise indicated.

EXAMPLE

For the first stage of the methylolation there is continuously introduced into a first reaction vessel, equipped with thermometer, a stirrer, a water jacket for heating and cooling, an electrode for pH control and a pump, a 50–56% aqueous solution of formaldehyde and melamine in a mole ratio of 15/1. The pH is maintained at about 5.0–5.5 and the temperature at about 65°–70° C. The residence time is controlled at about 60 minutes whereby the melamine becomes methylolated to an average degree of about 5.0 in an amount of about 40% in the monomeric state and about 60% in the oligomer state.

For the second stage of the methylolation, the reaction mixture is pumped continuously from the first reactor into a second reactor that is comparable to the first, but the pH controller is adjusted so as to add sufficient caustic to maintain the pH at about 8.5–9.0. The temperature is held at about the same temperature as in the first reactor and the residence time is adjusted to about 90 minutes so that a methylation level dictated by the equilibrium concentration is obtained at steady state. Typically, analysis of the reaction mixture at this stage shows about 5.7–5.8 moles of formaldehyde combined per mole of melamine.

The reaction mixture from the second reactor is passed to a vacuum evaporator where it is concentrated by removal of about 80% of its water content, the condensed water removed containing about 10% formaldehyde.

The mixture is withdrawn from the concentrator and pumped into a third reactor along with a sufficient amount of methanol to provide about 25 moles of methanol per mole of melamine. This reactor is operated at a pH of 2.0 by controlled addition of an acid such as nitric acid, and at a temperature of about 45° C. and a residence time of about 60 minutes. The product formed in this reactor has a combined melamine to formaldehyde to methanol mole ratio of about 1:5.7–5.8:4.7–5.0.

The partially methylated reaction mixture is passed from the third reactor to a neutralization tank where the pH thereof is adjusted to 11. From the neutralization tank, the reaction mixture is passed continuously to a distillation column for recovery of unreacted methanol.

The bottoms from the distillation column are pumped continuously to a (first) stripper for removal of substantially all the water and unreacted formaldehyde. The concentrated reaction mixture is then pumped into a fourth reactor along with about 5 additional moles of methanol per mole of melamine in order to raise the methylation level of the product. This fourth reactor is operated at a pH of about 2.0 and a temperature of about 35° C. The residence time is about 60 minutes. The reaction product mixture leaving this reactor contains unreacted methanol and formaldehyde plus water and salts. The methanol and water are stripped off (second stripper) after neutralization to a pH of about 9, and the recovered methanol has a quality suitable for recycling. The bottoms from the stripper consist of the substantially completely methylated, substantially completely methlolated melamine product and precipitated sodium nitrate and sodium formate salts. The latter are removed by treatment in a rotary vacuum filter to provide a resin of the desired clarity.

On analysis, the filtered product, a clear and colorless liquid, contains an average of 5.8 to 5.9 moles of combined formaldehyde per mole of melamine, an average of 5.2 to 5.4 moles of combined methanol per mole of melamine; 60±5% monomer, 20±5% dimer and 20±5% trimer and higher oligomers. The Gardner-Holdt viscosity of the product varies between X and $Z_2$ at 25° C.

Certain preferred, but not imperative, embodiments of the invention involve a recycling of the methanol obtained from the methanol recovery distillation column (step 5) back to the third reactor (step 3). Also, the water and the unreacted formaldehyde removed in the first stripper may be recycled back to the first reactor. Still further, the volatiles removed in the second stripper may be recycled back to the third reactor. All of these recycling embodiments are economically preferred.

We claim:

1. A continuous process for making a substantially fully methylated, substantially fully methylolated melamine composition comprising the steps of:

(1) conducting the methylolation of melamine in two stages as follows: (a) in a first stage, continuously charging melamine and aqueous formaldehyde to a first reaction zone in a ratio of from about 9 to about 18 moles of formaldehyde per mole of melamine while controlling the pH of the reaction mixture thus formed in the reaction zone at from about 4 to 6 and also controlling the temperature of the reaction mixture at from about 45° C. to about 75° C. and the residence time of the mixture in said zone for a period sufficiently long to allow the melamine to become methylolated to an average of about 4.5 to 5.5, said methylolated product being from about 40% to about 70% in the oligomeric state and from about 30% to about 60% in the monomeric state, then (b), in a second stage, passing the reaction mixture from the first reaction zone to a second reaction zone and adjusting the pH of the mixture in the second zone to from above 7 to about 10 and holding the temperature at about 45° C. to about 75° C. for a residence time sufficient for the melamine monomers and oligomers to become substantially fully methylolated;

(2) withdrawing the methylolated reaction mixture from the second reactor and removing about 70–95% of the water content thereof;

(3) passing the concentrated reaction mixture to a third reaction zone along with from about 20 to about 30 moles of methanol per mole of melamine utilized in step 1(a) while controlling the pH of the mixture at from about 1.2 to about 2.5, the temperature of the reaction mixture at from about 30° C. to about 55° C. and the residence time of the mixture in the reaction zone for a period sufficient to effect an average degree of methylation of the methylolmelamine of at least 4.5;

(4) withdrawing the reaction mixture from the third reaction zone into a neutralization zone and adjusting the pH thereof to from about 9 to 12;

(5) withdrawing the mixture from the neutralization zone to a distillation column and distilling off unreacted methanol therefrom;

(6) passing the bottoms from the distillation column to a stripping zone and stripping off substantially all of the water and unreacted formaldehyde therefrom; and (7) treating the bottoms from step 6 in a solids separation unit to remove precipitated salts therefrom and provide the substantially fully methylated, substantially fully methylolated melamine composition product.

2. A continuous process for making a substantially fully methylated, substantially fully methylolated melamine composition comprising the steps of:

(1) conducting the methylolation of melamine in two stages as follows: (a) in a first stage, continuously charging melamine and aqueous formaldehyde to a first reaction zone in a ratio of from about 9 to about 18 moles of formaldehyde per mole of melamine while controlling the pH of the reaction mixture thus formed in the reaction zone at from about 4 to 6 and also controlling the temperature of the reaction mixture at from about 45° C. to about 75° C. and the residence time of the mixture in said zone for a period sufficiently long to allow the melamine to become methylolated to an average of about 4.5 to 5.5, said methylolated product being from about 40% to about 70% in the oligomeric state and from about 30% to about 60% in the monomeric state, then (b), in a second stage, passing the reaction mixture from the first reaction zone to a second reaction zone and adjusting the pH of the mixture in the second zone to from above 7 to about 10 and holding the temperature at about 45° C. to about 75° C. for a residence time sufficient for the melamine monomers and oligomers to become substantially fully methylolated;

(2) withdrawing the methylolated reaction mixture from the second reactor and removing about 70–95% of the water content thereof;

(3) passing the concentrated reaction mixture to a third reaction zone along with from about 20 to about 30 moles of methanol per mole of melamine utilized in step 1(a) while controlling the pH of the mixture at from about 1.2 to about 2.5, the temperature of the reaction mixture at from about 30° C. to about 55° C. and the residence time of the mixture in the reaction zone for a period sufficient to effect an average degree of methylation of the methylolmelamine of at least 4.5;

(4) withdrawing the reaction mixture from the third reaction zone into a first neutralization zone and adjusting the pH thereof to from about 9 to 12;

(5) withdrawing the mixture from the neutralization zone to a distillation column and distilling off unreacted methanol therefrom;

(6) passing the bottoms from the distillation column to a first stripping zone and stripping off substantially all of the water and unreacted formaldehyde therefrom;

(7) passing the bottoms from the first stripping zone to a fourth reaction zone along with sufficient methanol to provide about 5–10 additional moles of methanol per mole of melamine used in step 1(a) and controlling the pH of the mixture at 1.2–2.5, the temperature at from about 30° C. to about 55° C. and the residence time to a period sufficient to give an average degree of methylation of at least 5.3;

(8) passing the reaction mixture from the fourth reactor to a second neutralization zone and adjusting the pH thereof to about 8–10;

(9) passing the reaction mixture from the second neutralization zone to a second stripping zone and stripping off all the volatiles therefrom and finally

(10) treating the bottoms from the second stripping zone in a solids separation unit to remove precipitated salts therefrom and provide the substantially fully methylated, substantially fully methylolated melamine composition product.

3. A process of making a substantially fully methylolated melamine comprising methylolating melamine in two stages as follows:

(a) in a first stage, charging melamine and aqueous formaldehyde to a first reaction zone while controlling the pH of the reaction mixture thus formed in the reaction zone to be acidic and the residence time of the mixture in said zone for a period sufficiently long to allow the melamine to become methylolated to an average of about 4.5 to 5.5, said methylolated product being from about 40 to 70 percent by weight in the oligomeric state and from about 60 to 30 percent by weight in the monomeric state, then (b) in a second stage, passing the reaction mixture from the first reaction zone to a second reaction zone and adjusting the pH of the mixture to be alkaline for a residence time sufficient for the melamine monomers and oligomers to become substantially fully methylolated.

4. The process of claim 3 wherein the ratio of formaldehyde to melamine is from about 9:1 to about 18:1.

5. The process of claim 3 wherein the pH of the first stage is about 4 to 6.

6. The process of claim 3 wherein the pH of the second stage is about above 7 to about 10.

7. The process of claim 3 wherein the temperature of each stage is about 45° to 75° C.

8. The process of claim 3 wherein the ratio of formaldehyde to melamine is from about 9:1 to about 18:1 and the temperature of each stage is about 45° to 75° C.

9. The process of claim 8 wherein the pH of the first stage is about 4 to 6 and the pH of the second stage is about above 7 to about 10.

10. The process of claims 3, or 8, or 9 wherein the process is conducted continuously.

11. The process of claims 3, or 8, or 9 wherein the methylolated melamine reaction mixture is substantially fully methylated by further reaction thereof with methanol.

* * * * *